United States Patent
Desos et al.

(10) Patent No.: US 7,253,162 B2
(45) Date of Patent: Aug. 7, 2007

(54) BENZOTHIAZINE AND BENZOTHIADIAZINE COMPOUNDS

(75) Inventors: Patrice Desos, Bois-Colombes (FR); Alex Cordi, Suresnes (FR); Pierre Lestage, La Celle Saint Cloud (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 25 days.

(21) Appl. No.: 10/865,184

(22) Filed: Jun. 10, 2004

(65) Prior Publication Data

US 2004/0254161 A1   Dec. 16, 2004

(30) Foreign Application Priority Data

Jun. 13, 2003 (FR) ................... 03 07117

(51) Int. Cl.
 C07D 513/04 (2006.01)
 A61K 31/542 (2006.01)
 A61P 25/24 (2006.01)

(52) U.S. Cl. ........................ 514/222.8; 544/9
(58) Field of Classification Search ............ 544/9; 514/222.8, 215; 540/578
See application file for complete search history.

(56) References Cited

OTHER PUBLICATIONS

Alt et al. Current Pharmaceutical Design, 2005, 11, 1511-1527.*
Black et al Psychopharmacology (2005) 179: 154-163.*
Daniel DeNoon, Schizophrenia Drug Face-Off: No Clear Winner, from the website http://www.webmd.com/content/Article/112/110297.htm?printing=true, downloaded on May 22, 2006.*
Maskell, et al., *Br. J. Pharmacol*, 2003, 140, 1313-1319.
Aracava, et al., *JPET*, 2005, 312, 1195-1250.
Advokat, et al., *Neurosci. Biobehav. Rev.*, 1992, 16, 13-24.
Danysz, et al., *Behav. Pharmacol.*, 1995, 6, 455-474.
Lynch, *Neurobiology of Learning and Memory*, 1998, 70, 82-100.
Robbins, et al., *TRENDS in Pharmacological Sciences*, 2006, 27 (3), 141-148.
Bliss, et al., *Nature*, 1993, 361, 31-39.
Ito, et al., *Journal of Physiology*, 1990, 424, 533-543.
Cumin, et al., *Psychopharmacology*, 1982, 78, 104-111.
Arai, et al., *Brain Res.*, 1994, 638, 343-346.
Miu, et al., *Neuropharmacol.*, 2001, 40, 976-983.
Staubli, et al., *Proc. Natl. Acad. Sci.*, 1994, 91, 777-781.
Lebrun, et al., *European Journal of Pharmacology*, 2000, 401, 205-212.
Rao, et al., *Neuroscience Letters*, 2001, 298, 183-186.
Thompson, et al., *Proc. Natl. Acad. Sci.*, 1995, 92, 7667-7671.
Buccafusco, et al., *Neuropharmacol.*, 2004, 46, 10-22.
Porrino, et al., *PLOS Biology*, 2005, 3 (9), 1639-1652.
Ingvar, et al., *Exp. Neurol.*, 1997, 146, 553-559.
Lynch, et al., *Exp. Neurol.*, 1997, 145, 89-92.
Baudry, *Neurobiology of Learning and Memory*, 2001, 76, 284-297.
Day, et al., *Nature*, 2003, 424, 205-209.
Lynch, *Current Opinion in Pharmacology*, 2006, 6, 82-88.
Lin, et al., *Brain Research*, 2002, 955, 164-173.
Desai, et al., *Neuropharmacology*, 1995, 34 (2), 141-147.
Lockhart, et al., *European Journal of Pharmacology*, 2000, 401, 145-153.
Jhee, et al., *J. Clin. Pharmacol.*, 2006, 46, 424-432.
Roger, et al., *Soc. Neurosci. Abstr.*, 2004, Abstract No. 219.11.
Dicou, et al., *Brain Research*, 2003, 970, 221-225.
Bahr, et al., *Exp. Neurol.*, 2002, 174, 37-47.
Murray, et al., *JPET*, 2003, 306, 752-762.
O'Neill, et al., *European Journal of Pharmacology*, 2004, 486, 163-174.
O'Neill, et al., *CNS Drug Rev.*, 2005, 11 (1), 77-96.
Bai, et al., *Neuropharmacology*, 2003, 44, 1013-1021.
Lauterborn, et al., *J. of Neuroscience*, 2000, 20 (1), 8-21.
Carrié, et al., *Soc. Neurosci. Abstr.*, 2005, Abstract No. 1018.4.
Lockhart, et al., *Soc. Neurosci. Abstr.*, 2004, Abstract No. 92.12.
Munoz, et al., *Soc. Neurosci. Abstr.*, 2004, Abstract No. 85.13.

(Continued)

Primary Examiner—Kahsay Habte
(74) Attorney, Agent, or Firm—Hueschen and Sage

(57) ABSTRACT

Compounds of formula (I):

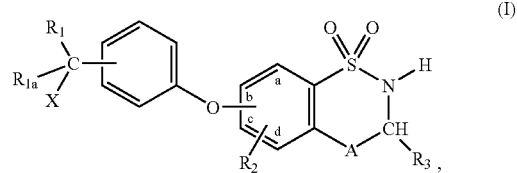

wherein:
 $R_1$ represents hydrogen, a halogen or alkyl,
 $R_{1a}$ represents hydrogen or alkyl,
 $R_2$ represents hydrogen, a halogen or hydroxy,
 A represents $CR_4R_5$ or $NR_4$,
 $R_3$ represents hydrogen, alkyl or cycloalkyl,
 $R_4$ represents hydrogen or alkyl,
or
 A represents nitrogen and, together with the adjacent —$CHR_3$—, forms the ring

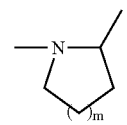

wherein m represents 1, 2 or 3,
 $R_5$ represents hydrogen or a halogen,
 X is as defined in the description,
their isomers, and also addition salts thereof.

13 Claims, No Drawings

OTHER PUBLICATIONS

Nibuya, et al., *J. of Neuroscience,* 1995, 15 (11), 7539-7547.
Dias, et al., *Neuropharmacology,* 2003, 45, 553-563.
Alt, et al., *Curr. Pharm. Des.,* 2005, 11 (12), 1511-1527.
Alt, et al., *Biochemical Pharmacology,* 2006, 71, 1273-1288.
Nakamura, et al., *Psychopharmacology,* 2001, 158, 205-212.
Li, et al., *Neuropharmacology,* 2001, 40, 1028-1033.
Knapp, et al., *European Journal of Pharmacology,* 2002, 440, 27-35.

* cited by examiner

BENZOTHIAZINE AND BENZOTHIADIAZINE COMPOUNDS

FIELD OF THE INVENTION

The present invention relates to new benzothiazine and benzothiadiazine compounds, to a process for their preparation and to pharmaceutical compositions containing them. The compounds of the present invention are new and have very valuable pharmacological properties in respect of AMPA receptors.

BACKGROUND OF THE INVENTION

It has now been recognised that the excitatory amino acids, especially glutamate, play a crucial role in the physiological processes of neuronal plasticity and in the mechanisms underlying learning and memory. Pathophysiological studies have clearly shown that a deficit in glutamatergic neurotransmission is closely linked to the development of Alzheimer's disease (Neuroscience and Biobehavioral reviews, 1992, 16, 13-24; Progress in Neurobiology, 1992, 39, 517-545).

In addition, innumerable works have in recent years demonstrated the existence of sub-types of excitatory amino acid receptors and their functional interactions (Molecular Neuropharmacology, 1992, 2, 15-31).

Among those receptors, the AMPA (α-amino-3-hydroxy-5-methyl-4-isoxazole-propionic acid) receptor appears to be involved to the greatest extent in the phenomena of physiological neuronal excitability and, especially, in those phenomena involved in memorisation processes. For example, it has been shown that learning is associated with an increase in the binding of AMPA to its receptor in the hippocampus, one of the areas of the brain essential to processes of memory and cognition. Likewise, nootropic agents such as aniracetam have very recently been described as modulating the AMPA receptors of neuronal cells in a positive manner (Journal of Neurochemistry, 1992, 58, 1199-1204).

DESCRIPTION OF THE PRIOR ART

In the literature, compounds having a benzamide structure have been described as possessing this same mechanism of action and improving memory performance (Synapse, 1993, 15, 326-329). Compound BA 74, in particular, is the most active of those new pharmacological agents.

Finally, patent specification EP 692 484 describes a benzothiadiazine compound having a facilitating action on the AMPA current, and patent application WO 99/42456 describes inter alia particular benzothiadiazine compounds as modulators of AMPA receptors.

The benzothiazine and benzothiadiazine compounds to which the present invention relates, besides being new, surprisingly exhibit pharmacological activity on the AMPA current that is markedly superior to the activity of the compounds having similar structures described in the prior art. They are useful as AMPA modulators for the treatment or prevention of disorders of memory and cognition that are associated with age, with syndromes of anxiety or depression, with progressive neurodegenerative diseases, with Alzheimer's disease, with Pick's disease, with Huntington's chorea, with schizophrenia, with the sequelae of acute neurodegenerative diseases, with the sequelae of ischaemia and with the sequelae of epilepsy.

DETAILED DESCRIPTION OF THE INVENTION

More specifically, the present invention relates to compounds of formula (I):

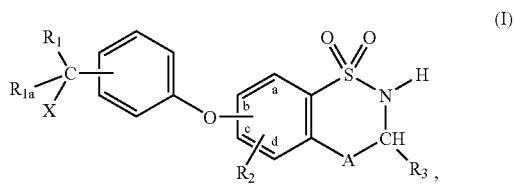

wherein:
$R_1$ represents a hydrogen atom, a halogen atom or a linear or branched ($C_1$-$C_6$)alkyl group,
$R_{1a}$ represents a hydrogen atom or a linear or branched ($C_1$-$C_6$)alkyl group,
$R_2$ represents a hydrogen atom, a halogen atom or a hydroxy group,
A represents a $CR_4R_5$ group or an $NR_4$ group,
$R_3$ represents a hydrogen atom, a linear or branched ($C_1$-$C_6$)alkyl group or a ($C_3$-$C_7$)cycloalkyl group,
$R_4$ represents a hydrogen atom or a linear or branched ($C_1$-$C_6$)alkyl group, or A represents a nitrogen atom and, together with the adjacent —$CHR_3$— group, forms the ring

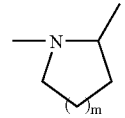

wherein m represents 1, 2 or 3,
$R_5$ represents a hydrogen or halogen atom,
X represents an $NR_6R_7$, $S(O)_nR_8$ or $OR'_8$ group or a heterocyclic group, wherein:
  $R_6$ represents a hydrogen atom, a linear or branched ($C_1$-$C_6$)alkyl group, $S(O)_pR_9$, $COR_9$ or $P(O)OR_9OR_{10}$,
  $R_7$ represents a hydrogen atom or a linear or branched ($C_1$-$C_6$)alkyl group, or $R_6$ and $R_7$, together with the nitrogen atom carrying them, form a heterocyclic group,
  $R_8$, $R_9$ and $R_{10}$, which may be the same or different, represent a hydrogen atom; a linear or branched ($C_1$-$C_6$)alkyl group optionally substituted by one or more halogen atoms; an aryl-($C_1$-$C_6$)alkyl group in which the alkyl moiety is linear or branched; or an aryl group,
  $R'_8$ represents a linear or branched ($C_1$-$C_6$)alkyl group or a linear or branched ($C_1$-$C_6$)acyl group,
  n and p, which may be the same or different, represent 1 or 2, to their enantiomers and diastereoisomers, and also to addition salts thereof with a pharmaceutically acceptable acid or base, it being understood that:
  a heterocyclic group means a monocyclic or bicyclic, aromatic or non-aromatic group containing from one to four identical or different hetero atoms selected from nitrogen, oxygen and sulphur, optionally substituted by one or more identical or different groups selected from halogen, linear or branched ($C_1$-$C_6$)alkyl, linear or branched ($C_1$-$C_6$)alkoxy, linear or branched ($C_1$-$C_6$)polyhaloalkyl, linear or branched ($C_1$-$C_6$)alkoxy-carbonyl, oxo, thioxo, carboxy, linear or branched ($C_1$-$C_6$)acyl, linear or branched ($C_1$-$C_6$)polyhaloalkoxy, hydroxy, cyano, nitro, amino (optionally substituted by one or more linear or branched ($C_1$-$C_6$)alkyl groups), aminosulphonyl (optionally substituted by one or more linear or branched ($C_1$-$C_6$)alkyl groups) and ($C_1$-$C_6$)alkylsulphonylamino, an aryl group is understood to mean a monocyclic aromatic group or a bicyclic group in which at least one of the rings is aromatic, optionally substituted by one or more identical or different groups selected from halogen, linear or branched ($C_1$-$C_6$)alkyl (optionally substituted by one or more hydroxy groups), linear or branched ($C_1$-$C_6$)alkoxy, linear or branched ($C_1$-$C_6$)polyhaloalkyl, linear or branched ($C_1$-$C_6$)alkoxy-carbonyl, oxo, thioxo, linear or branched ($C_1$-$C_6$)alkylthio, carboxy, linear or branched ($C_1$-$C_6$)acyl, linear or branched ($C_1$-$C_6$)polyhaloalkoxy, hydroxy, cyano, nitro, amino (optionally substituted by one or more linear or branched ($C_1$-$C_6$)alkyl or linear or branched ($C_1$-$C_6$)acyl groups), aminocarbonyl (optionally substituted by one or more linear or branched ($C_1$-$C_6$)alkyl groups), aminosulphonyl (optionally substituted by one or more linear or branched ($C_1$-$C_6$)alkyl groups), mono- or di-(($C_1$-$C_6$)alkylsulphonyl)amino, mono- or di-(trifluoromethylsulphonyl)amino, PO(O$R_a$)(O$R_b$) (wherein $R_a$ and $R_b$, which may be the same or different, represent a hydrogen atom or a linear or branched ($C_1$-$C_6$)alkyl group), benzyloxy and phenyl (optionally substituted by one or more identical or different groups selected from halogen, linear or branched ($C_1$-$C_6$)alkyl, linear or branched ($C_1$-$C_6$)perhaloalkyl, hydroxy and linear or branched ($C_1$-$C_6$)alkoxy).

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

The grouping

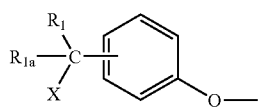

is preferably in position b of the phenyl carrying it.

Preference is given to the $R_{1a}$ and $R_2$ groups being hydrogen atoms.

The grouping

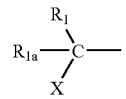

is preferably in the meta- or para-position of the phenoxy ring structure carrying it.

X preferably represents an $NR_6R_7$ or $S(O)_nR_8$ group or a heterocyclic group.

More especially, the group X is preferably the $NR_6R_7$ group wherein $R_6$ represents a hydrogen atom or an $S(O)_pR_9$ group and $R_7$ represents a hydrogen atom, such as, for example, the groups $NHSO_2Me$, $NHSO_2iPr$, $NHSO_2CF_3$, $NH_2$.

Preferred compounds of the invention are compounds wherein; A represents a nitrogen atom and, together with the adjacent —$CHR_3$— group, forms the ring

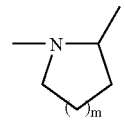

wherein m represents 1, 2 or 3, preferably 1.

Preferred compounds of the invention are:
{3-[(5,5-dioxido-2,3,3a,4-tetrahydro-1H-pyrrolo[2,1-c][1,2,4]benzothiadiazin-7yl)-oxy]phenyl}methanamine,
N-{3-[(5,5-dioxido-2,3,3a,4-tetrahydro-1H-pyrrolo[2,1-c][1,2,4]benzothiadiazin-7-yl)-oxy]benzyl}methanesulphonamide,
N-{4-[(5,5-dioxido-2,3,3a,4-tetrahydro-1H-pyrrolo[2,1-c][1,2,4]benzothiadiazin-7yl)-oxy]benzyl}methanesulphonamide.

The invention relates also to the processes for the preparation of compounds of formula (I).

The process for the preparation of compounds of formula (I) wherein A represents an $NR_4$ group or A represents a nitrogen atom and, together with the adjacent $CHR_3$ group, forms the ring

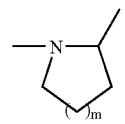

wherein m represents 1, 2 or 3, is characterised in that there is used as starting material a compound of formula (II):

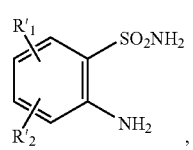

(II)

wherein:

R'$_1$ represents a linear or branched (C$_1$-C$_6$)alkoxy group,

R'$_2$ represents a hydrogen atom, a halogen atom or a linear or, branched (C$_1$-C$_6$)alkoxy group, which is:

(a) either reacted with the acid chloride of formula (III) in the presence of a base, in a tetrahydrofuran or acetonitrile medium:

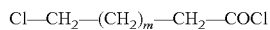 (III), wherein m is as defined for formula (I), to yield the compound of formula (IV):

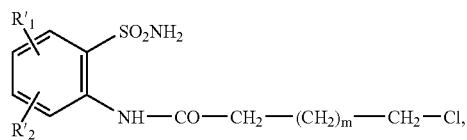 (IV)

wherein R'$_1$ and R'$_2$ are as defined hereinbefore, which is then cyclised in a basic medium to yield the compound of formula (V):

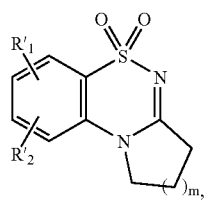 (V)

wherein R'$_1$, R'$_2$ and mn are as defined hereinbefore, which is optionally subjected to reduction, in an alcoholic or dimethylformamide medium, in the presence of sodium borohydride, to yield the compound of formula (VI):

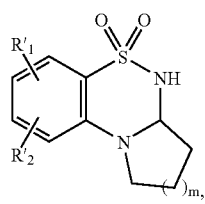 (VI)

wherein R'$_1$, R'$_2$ and mn are as defined hereinbefore, which compound of formula (V) or (VI) is subjected to the action of boron tribromide to yield the compound of formula (VII):

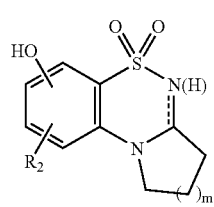 (VII)

wherein R$_2$ is as defined for formula (I) and mn is as defined hereinbefore, (b) or cyclised:
in the presence of an amidine of formula (VIII):

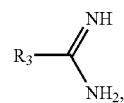 (VIII)

wherein R$_3$ is as defined for formula (I), to yield the compound of formula (IX):

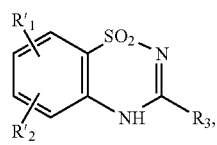 (IX)

wherein R'$_1$, R'$_2$ and R$_3$ are as defined hereinbefore, which is:
either reduced, using a metallic hydride,
to yield the compound of formula (X):

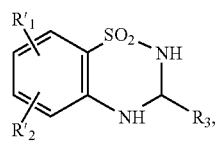 (X)

wherein R'$_1$, R'$_2$ and R$_3$ are as defined hereinbefore, or alkylated by the action of a strong base in the presence of an alkylating agent R'$_4$X, wherein R'$_4$ represents a linear or branched (C$_1$-C$_6$)alkyl group and X represents a halogen atom, and then reduced to yield the compound of formula (XI):

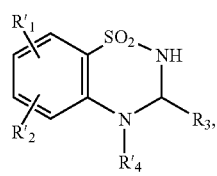 (XI)

wherein R'$_1$, R'$_2$, R$_3$ and R'$_4$ are as defined hereinbefore,
in the presence of an aldehyde of formula (XII):

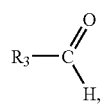 (XII)

wherein R$_3$ is as defined for formula (I), to yield the compound of formula (X) described hereinbefore, in which compound of formula (X) or (XI) the group R'$_1$ and, when the group R'$_2$ represents a linear or branched (C$_1$-C$_6$)alkoxy group, the group R'$_2$ are converted into hydroxy groups to yield the compound of formula (XIII):

(XIII)

wherein R$_2$, R$_3$ and R$_4$ are as defined for formula (I), which compound of formula (VII) or (XIII) is reacted with a boronic acid compound of formula (XIV):

(XIV)

wherein R''$_1$ represents a cyano group or an R$_1$R$_{1a}$XC— group as defined for formula (I), to yield (after optional conversion of the group R''$_1$, when the latter represents a cyano group, into an NR$_6$R$_7$ group as defined for formula (I)) the compound of formula (I/a$_1$) or (I/a$_2$), particular cases of the compounds of formula (I):

(I/a$_1$)

wherein R$_1$, R$_{1a}$, R$_2$, R$_3$, R$_4$ and X are as defined for formula (I), (I/a$_2$)

wherein R$_1$, R$_{1a}$, R$_2$, m and X are as defined for formula (I), which compounds of formulae (I/a$_1$) and (I/a$_2$):

are purified, if necessary, according to a conventional purification technique, are separated, if desired, into their isomers according to a conventional separation technique and are converted, if desired, into their addition salts with a pharmaceutically acceptable acid or base.

The process for the preparation of compounds of formula (I) wherein A represents a CR$_4$R$_5$ group is characterised in that there is used as starting material a compound of formula (XV):

(XV)

wherein:
R'$_1$ represents a linear or branched (C$_1$-C$_6$)alkoxy group,
R'$_2$ represents a hydrogen atom, a halogen atom or a linear or branched (C$_1$-C$_6$)alkoxy group, which is subjected to the action of chloroacetone in the presence of dimethylformamide to yield the compound of formula (XVI)

(XVI)

wherein R'$_1$ and R'$_2$ are as defined hereinbefore, which is subjected to a rearrangement in a basic medium to yield the compound of formula (XVII):

(XVII)

wherein R'$_1$ and R'$_2$ are as defined hereinbefore, is deacetylated by heating at reflux in a benzene medium in the presence of an excess of ethylene glycol and a catalytic amount of p-toluenesulphonic acid to yield the compound of formula (XVIII):

(XVIII)

wherein R'$_1$ and R'$_2$ are as defined hereinbefore, which is subjected to hydrolysis in an acid medium to yield the compound of formula (XIXa):

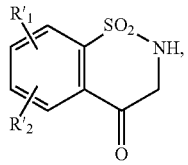

(XIXa)

wherein R'$_1$ and R'$_2$ are as defined hereinbefore, the nitrogen atom of which is optionally, depending on the nature of the group R$_3$ that is desired, protected by a protecting group and which is then, after treatment with a strong base, treated with a compound of formula R'$_3$—P, wherein R'$_{13}$ represents a linear or branched (C$_1$-C$_6$)alkyl group or a (C$_3$-C$_7$)cycloalkyl group and P represents a leaving group, to yield, after deprotection of the nitrogen atom, the compound of formula (XIX'a):

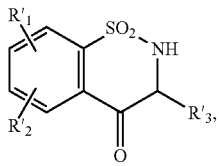

(XIX'a)

wherein R'$_1$, R'$_2$ and R'$_3$ are as defined hereinbefore, which compound of formula (XIXa) or (XIX'a), represented by formula (XIX):

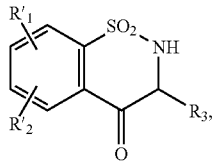

(XIX)

wherein R'$_1$ and R'$_2$ are as defined hereinbefore and R$_3$ is as defined for formula (I), is:

either subjected to catalytic reduction to yield the compound of formula (XX):

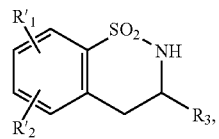

(XX)

wherein R'$_1$ and R'$_2$ are as defined hereinbefore,
or converted by the action of a hydride into an alcohol, the hydroxy group of which is converted into a halogen atom by the action of an appropriate reagent to yield the compound of formula (XXI):

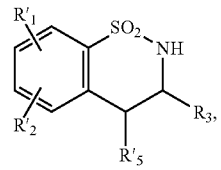

(XXI)

wherein R'$_1$, R'$_2$ and R$_3$ are as defined hereinbefore and R'$_5$ represents a halogen atom, or subjected to the action of an organomagnesium compound R'$_4$MgBr, wherein R'$_4$ represents a linear or branched (C$_1$-C$_6$)alkyl group, to yield the compound of formula (XIXb):

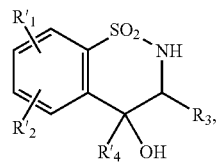

(XIXb)

wherein R'$_1$, R'$_2$, R$_3$ and R'$_4$ are as defined hereinbefore, which compound of formula (XIXb)
either is subjected to catalytic reduction to yield the compound of formula (XXII):

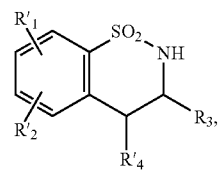

(XXII)

wherein R'$_1$, R'$_2$, R$_3$ and R'$_4$ are as defined hereinbefore,
or the hydroxy group thereof is converted into a halogen atom by the action of an appropriate reagent to yield the compound of formula (XXIII):

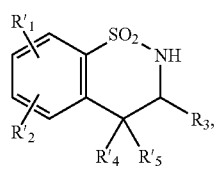

(XXIII)

wherein R'$_1$, R'$_2$, R$_3$ and R'$_4$ are as defined hereinbefore and R'$_5$ represents a halogen atom, in which compounds of formulae (XX) to (XXIII) the group R'$_1$ and, when the group R'$_2$ represents a linear or branched (C$_1$-C$_6$)alkoxy group, the group R'$_2$ are converted into hydroxy groups to yield the compound of formula (XXIV):

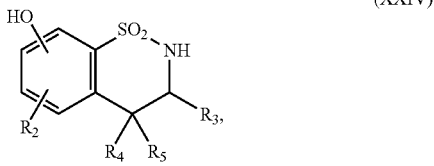

(XXIV)

wherein $R_2$, $R_3$, $R_4$ and $R_5$ are as defined for formula (I), which compound of formula (XXIV) is reacted with a boronic acid compound of formula (XIV):

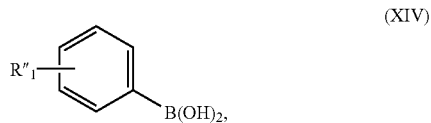

(XIV)

wherein $R''_1$ represents a cyano group or an $R_1R_{1a}XC—$ group as defined for formula (I), to yield (after optional conversion of the group $R''_1$, when the latter represents a cyano group, into an $NR_6R_7$ group as defined for formula (I)) the compound of formula (I/b), a particular case of the compounds of formula (I):

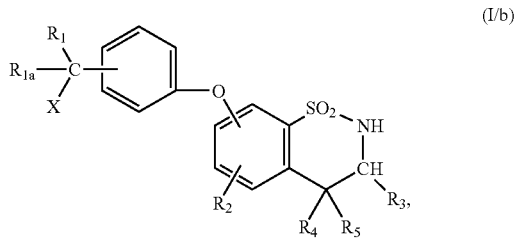

(I/b)

wherein $R_1$, $R_{1a}$, $R_2$, $R_3$, $R_4$, $R_5$ and X are as defined for formula (I), which compound of formula (I/b) is purified, if necessary, according to a conventional purification technique, is separated, if desired, into its isomers according to a conventional separation technique and is converted, if desired, into its' addition salts with a pharmaceutically acceptable acid or base.

The invention relates also to pharmaceutical compositions comprising, as active ingredient, a compound of formula (I) with one or more appropriate, inert, non-toxic excipients. Among the pharmaceutical compositions according to the invention there may be mentioned more especially those that are suitable for oral, parenteral (intravenous or subcutaneous) or nasal administration, tablets or dragées, sublingual tablets, gelatin capsules, lozenges, suppositories, creams, ointments, dermal gels, injectable preparations, drinkable suspensions etc.

The useful dosage can be varied according to the nature and severity of the disorder, the administration route and the age and weight of the patient and ranges from 1 to 500 mg per day in one or more administrations.

The Examples that follow illustrate the invention but do not limit it in any way.

The starting materials used are products that are known or that are prepared according to known operating procedures.

The structures of the compounds described in the Examples were determined according to the usual spectrophotometric techniques (infrared, NMR, mass spectrometry, . . . ).

EXAMPLE 1

{3-[(5,5-Dioxido-2,3,3a,4-tetrahydro-1H-pyrrolo[2,1-c][1,2,4]-benzothiadiazin-7-yl)oxy]phenyl}methanamine hydrochloride Step A: 2,3-Dihydro-1H-pyrrolo[2,1-c][1,2,4]benzothiadiazin-7-ol 5,5-dioxide A solution of $BBr_3$ (68.75 mmol) in 25 ml of methylene chloride is added dropwise to a solution, cooled to 0° C., of 27.5 mmol of 7-methoxy-2,3-dihydro-1H-pyrrolo[2,1-c]-[1,2,4]benzothiadiazine 5,5-dioxide in 350 ml of methylene chloride. Stirring is carried out at ambient temperature for 24 hours. The reaction mixture is poured into a mixture of ice and water, and the suspension is stirred for 30 minutes. The precipitate is filtered off, rinsed several times with water, filtered under suction and dried in vacuo to yield the expected product.

Melting point: >300° C. Elemental micro-analysis:

|  | C % | H % | N % | S % |
|---|---|---|---|---|
| Calculated | 50.41 | 4.23 | 11.76 | 13.46 |
| Found | 50.00 | 4.19 | 11.28 | 13.41 |

Step B: 3-[(5,5-Dioxido-2,3-dihydro-1H-pyrrolo[2,1-c][1,2,4]benzothiadiazin-7-yl)-oxy]benzonitrile A suspension composed of 7.06 mmol of the product obtained in the Step above, 3-cyanophenylboronic acid (11.02 mmol), copper(II) acetate (11.02 mmol), pyridine (22.0 mmol) and about 500 mg of 4 Å molecular sieve in 200 ml of methylene chloride is stirred for 24 hours. The reaction mixture is diluted by adding a further 100 ml of methylene chloride and the suspension is filtered. The filtrate is concentrated and then directly placed on a silica column which is eluted with a methylene chloride/methanol 95/5 system. The fractions containing the expected product are combined and evaporated, and the residue is taken up in a small amount of ethyl ether. After filtering off the solid, the expected product is recovered in the form of a white powder.

Melting point: 229-233° C. Elemental micro-analysis:

|  | C % | H % | N % | S % |
|---|---|---|---|---|
| Calculated | 60.17 | 3.86 | 12.38 | 9.45 |
| Found | 59.42 | 3.96 | 12.29 | 9.63 |

Step C: {3-[(5,5-Dioxido-2,3,3a,4-tetrahydro-1H-pyrrolo[2,1-c][1,2,4]-benzothiadiazin-7-yl)oxy]phenyl)}methanamine hydrochloride 112 mg (2.95 mmol) of $LiAlH_4$ are added, in small portions, to a solution of 0.58 mmol of the product of the Step above in 20 ml of anhydrous THF and the mixture is stirred at ambient temperature for 1 hour. The excess of hydride is hydrolysed by the successive dropwise addition of 1.5 ml of isopropanol and 1.5 ml of saturated aqueous NaCl solution. The aluminium salts are filtered off and the filtrate is evaporated to dryness. The residue is chromatographed on a silica column, eluting with a mixture of $CH_2Cl_2$/EtOH/aq. $NH_3$ 95/5/0.5. After evaporating the fractions containing the amine, the meringue is taken up in ethereal HCl. The solution is evaporated to dryness and the residue is redissolved in a minimum of isopropanol. The expected product crystallises out and is recovered by filtration.

Melting point: 145° C. Elemental micro-analysis

|  | C % | H % | N % | S % | Cl % |
|---|---|---|---|---|---|
| Calculated | 53.47 | 5.28 | 11.00 | 8.40 | 9.28 |
| Found | 53.09 | 5.34 | 10.65 | 8.30 | 9.30 |

EXAMPLE 2

N-{3-[(5,5-Dioxido-2,3,3a,4-tetrahydro-1H-pyrrolo[2,1-c][1,2,4]-benzothiadiazin-7-yl)oxy]benzyl}methanesulphonamide Methanesulphonic anhydride (0.20 mmol) dissolved in 2 ml of $CH_2Cl_2$ is added dropwise to a solution, cooled in an ice-bath, of the compound obtained in Example 1 (0.136 mmol) in 10 ml of $CH_2Cl_2$ containing 0.34 mmol of $Et_3N$. The reaction mixture is stirred at ambient temperature for 3 hours. The reaction solution is washed with water and then with saturated NaCl and is dried over $MgSO_4$. After evaporation in vacuo, the residue is made more solid by triturating in ethyl ether to yield the title product after filtration.

Melting point: 183-190° C. Elemental micro-analysis.

|  | C % | H % | N % | S % |
|---|---|---|---|---|
| Calculated | 51.06 | 5.00 | 9.92 | 15.14 |
| Found | 51.09 | 5.33 | 9.58 | 15.55 |

The following Examples were prepared according to the procedures described in Examples 1 or 2, starting from appropriate starting materials.

EXAMPLE 3

N-{3-[(5,5-Dioxido-2,3,3a,4-tetrahydro-1H-pyrrolo[2,1-c][1,2,4]-benzothiadiazin-7-yl)oxy]benzyl}acetamide Melting point: 58° C. Elemental micro-analysis:

|  | C % | H % | N % | S % |
|---|---|---|---|---|
| Calculated | 58.90 | 5.46 | 10.85 | 8.28 |
| Found | 58.51 | 5.73 | 10.36 | 7.82 |

EXAMPLE 4

N-(1-{3-[(5,5-Dioxido-2,3,3a,4-tetrahydro-1H-pyrrolo[2,1-c][1,2,4]-benzothiadiazin-7-yl)oxy]phenyl}ethyl)acetamide

EXAMPLE 5

N-(1-{3-[(5,5-Dioxido-2,3,3a,4-tetrahydro-1H-pyrrolo[2,1-c][1,2,4]-benzothiadiazin-7-yl)oxy]phenyl}-1-fluoroethyl)acetamide

EXAMPLE 6

3-[(5,5-Dioxido-2,3,3a,4-tetrahydro-1H-pyrrolo[2,1-c][1,2,4]-benzothiadiazin-7-yl)oxy]benzyl isopropyl sulphone

EXAMPLE 7

1-{3-[(5,5-Dioxido-2,3,3a,4-tetrahydro-1H-pyrrolo[2,1-c][1,2,4]-benzothiadiazin-7-yl)oxy]phenyl}ethyl isopropyl sulphone

EXAMPLE 8

1-{3-[(5,5-Dioxido-2,3,3a,4-tetrahydro-1H-pyrrolo[2,1-c][1,2,4]-benzothiadiazin-7-yl)oxy]phenyl}-1-fluoroethyl isopropyl sulphone

EXAMPLE 9

N-{3-[(5,5-Dioxido-2,3,3a,4-tetrahydro-1H-pyrrolo[2,1-c][1,2,4]-benzothiadiazin-7-yl)oxy]benzyl}(trifluoro)methanesulphonamide Melting point: 104-113° C. Elemental Micro-Analysis:

|  | C % | H % | N % | S % |
|---|---|---|---|---|
| Calculated | 45.28 | 3.80 | 8.80 | 13.43 |
| Found | 46.20 | 3.87 | 8.58 | 13.84 |

EXAMPLE 10

N-(1-{3-[(5,5-Dioxido-2,3,3a,4-tetrahydro-1H-pyrrolo[2,1-c][1,2,4]-benzothiadiazin-7-yl)oxy]phenyl}ethyl)(trifluoro)methane-sulphonamide

EXAMPLE 11

N-(1-{3-[(5,5-Dioxido-2,3,3a,4-tetrahydro-1H-pyrrolo[2,1-c][1,2,4]-benzothiadiazin-7-yl)oxy]phenyl}11-fluoroethyl)(trifluoro)methane-sulphonamide

EXAMPLE 12

N-{3-[(5,5-Dioxido-2,3,3a,4-tetrahydro-1H-pyrrolo[2,1-c][1,2,4]-benzothiadiazin-7-yl)oxy]benzyl}-N-methylbenzamide

EXAMPLE 13

N-(1-{3-[(5,5-Dioxido-2,3,3a,4-tetrahydro-1H-pyrrolo [2,1-c][1,2,4]-benzothiadiazin-7-yl)oxy] phenyl}ethyl)-N-methylbenzamide

EXAMPLE 14

N-(1-{3-[(5,5-Dioxido-2,3,3a,4-tetrahydro-1H-pyrrolo [2,1-c][1,2,4]-benzothiadiazin-7-yl)oxy]phenyl}-1-fluoroethyl)-N-methylbenzamide

EXAMPLE 15

7-{[3-(1H-Imidazol-4-yl)methyl]phenoxy}-2,3,3a,4-tetrahydro-1H-pyrrolo[2,1-c][1,2,4]benzothiadiazine 5,5-dioxide

EXAMPLE 16

7-{3-[1-(1H-imidazol-4-yl)ethyl]phenoxy}-2,3,3a,4-tetrahydro-1H-pyrrolo[2,1-c][1,2,4]benzothiadiazine 5,5-dioxide

EXAMPLE 17

7-{3-[1-Fluoro-1-(1H-imidazol-4-yl)ethyl]phenoxy}-2,3,3a,4-tetrahydro-1H-pyrrolo[2,1-c][1,2,4] benzothiadiazine 5,5-dioxide

EXAMPLE 18

N-{3-[(5,5-Dioxido-2,3,3a,4-tetrahydro-1H-pyrrolo [2,1-c][1,2,4]-benzothiadiazin-7-yl)oxy] benzyl}propane-2-sulphonamide Melting point: 112-118° C. Elemental micro-analysis:

|  | C | H | N | S |
|---|---|---|---|---|
| Theoretical % | 53.20 | 5.58 | 9.31 | 14.20 |
| Empirical % | 53.36 | 5.80 | 9.24 | 14.52 |

EXAMPLE 19

7-[3-(1H-Pyrrol-1-ylmethyl)phenoxy]-2,3,3a,4-tetrahydro-1H-pyrrolo[2,1-c][1,2,4]benzothiadiazine 5,5-dioxide 200 mg (0.58 mmol) of the product obtained in Example 1, in the form of the free amine, and 105 μl (0.81 mmol) of 2,5-dimethoxytetrahydrofuran are added to a two-phase mixture of 2.5 ml of water, 0.95 ml of AcOH and 2.85 ml of dichloro-1,2-ethane. The mixture is stirred at 80° C. for 2 hours, allowed to return to ambient temperature and extracted with $CH_2Cl_2$. The organic phase is washed with saturated aqueous NaCl solution and dried over $MgSO_4$. The expected product is purified by chromatography on a silica column ($CH_2Cl_2$/heptane 75/25).

Melting point: 150-152° C. Elemental Micro-Analysis:

|  | C | H | N | S |
|---|---|---|---|---|
| Theoretical % | 63.78 | 5.35 | 10.63 | 8.11 |
| Empirical % | 63.65 | 5.28 | 10.38 | 8.41 |

EXAMPLE 20

1-{4-[(5,5-Dioxido-2,3,3a,4-tetrahydro-1H-pyrrolo [2,1-c][1,2,4]-benzothiadiazin-7-yl)oxy] phenyl}methanamine hydrochloride The procedure is as in Example 1, replacing the 3-cyanophenylboronic acid in Step B by the 4-cyanophenylboronic acid isomer.

Melting point: 165-172° C. Elemental micro-analysis:

|  | C | H | N | S | Cl |
|---|---|---|---|---|---|
| Theoretical % | 53.47 | 5.28 | 11.00 | 8.40 | 9.28 |
| Empirical % | 54.08 | 5.16 | 10.46 | 8.25 | 9.42 |

EXAMPLE 21

N-{4-[(5,5-Dioxido-2,3,3a,4-tetrahydro-1H-pyrrolo [2,1-c][1,2,4]-benzothiadiazin-7-yl)oxy] benzyl}methanesulphonamide The procedure is as in Example 2, starting from the compound obtained in Example 20.

Melting point: 104-110° C. Elemental micro-analysis:

|  | C | H | N | S |
|---|---|---|---|---|
| Theoretical % | 51.05 | 5.00 | 9.92 | 15.14 |
| Empirical % | 51.24 | 5.45 | 9.17 | 14.94 |

The 2 enantiomers of Example 21 were separated by chiral chromatography on a Chiralpak AD® column. Eluant: $CH_3CN$/iPrOH/DEA 1000/2/1. The 2 enantiomers are listed in Examples 22 and 23 in the order in which they are eluted under the above-mentioned conditions.

EXAMPLE 22

N-{4-[(5,5-Dioxido-2,3,3a,4-tetrahydro-1H-pyrrolo [2,1-c][1,2,4]-benzothiadiazin-7-yl)oxy] benzyl}methanesulphonamide, enantiomer 1

Elemental Micro-Analysis:

|  | C | H | N | S |
|---|---|---|---|---|
| Theoretical % | 51.05 | 5.00 | 9.92 | 15.14 |
| Empirical % | 50.48 | 5.08 | 9.63 | 15.53 |

EXAMPLE 23

N-{4-[(5,5-Dioxido-2,3,3a,4-tetrahydro-1H-pyrrolo[2,1-c][1,2,4]-benzothiadiazin-7-yl)oxy]benzyl}methanesulphonamide, enantiomer 2

Elemental Micro-Analysis:

|  | C | H | N | S |
|---|---|---|---|---|
| Theoretical % | 51.05 | 5.00 | 9.92 | 15.14 |
| Empirical % | 50.77 | 5.06 | 9.70 | 15.47 |

EXEMPLE 24

N-{4-[(5,5-Dioxido-2,3,3a,4-tetrahydro-1H-pyrrolo[2,1-c][1,2,4]-benzothiadiazin-7-yl)oxy]benzyl}acetamide The procedure is as in Example 2, replacing the methanesulphonic anhydride by acetyl chloride and using as starting material the amine obtained in Example 20.

Melting point: 158-161° C. Elemental micro-analysis:

|  | C | H | N | S |
|---|---|---|---|---|
| Theoretical % | 58.90 | 5.46 | 10.85 | 8.28 |
| Empirical % | 58.85 | 5.69 | 10.65 | 8.51 |

EXAMPLE 25

N-{4-[(5,5-Dioxido-2,3,3a,4-tetrahydro-1H-pyrrolo[2,1-c][1,2,4]-benzothiadiazin-7-yl)oxy] benzyl}-2,2,2-trifluoroacetamide The procedure is as in Example 2, replacing the methanesulphonic anhydride by trifluoroacetic anhydride and using as starting material the amine obtained in Example 20.

Melting point: 136-138° C. Elemental micro-analysis

|  | C | H | N | S |
|---|---|---|---|---|
| Theoretical % | 51.70 | 4.11 | 9.52 | 7.26 |
| Empirical % | 51.84 | 4.24 | 9.36 | 7.48 |

EXAMPLE 26

N-{3-[(5,5-Dioxido-2,3,3a,4-tetrahydro-1H-pyrrolo[2,1-c][1,2,4]-benzothiadiazin-7-yl)oxy]benzyl}-4-fluorobenzamide The procedure is as in Example 2, replacing the methanesulphonic anhydride by 4-fluorobenzoyl chloride and using as starting material the amine obtained in Example 20.

Melting point: 104-108° C. Elemental micro-analysis:

|  | C | H | N | S |
|---|---|---|---|---|
| Theoretical % | 61.66 | 4.74 | 8.99 | 6.86 |
| Empirical % | 61.41 | 4.81 | 8.72 | 6.66 |

EXAMPLE 27

7-[4-(1H-Tetrazol-5-ylmethyl)phenoxy]-2,3,3a,4-tetrahydro-1H-pyrrolo[2,1-c][1,2,4]benzothiadiazine 5,5-dioxide Step A: {4-[(5,5-Dioxido-2,3,3a,4-tetrahydro-1H-pyrrolo[2,1-c][1,2,4]benzothiadiazin-7-yl)oxy]phenyl}acetonitrile A suspension composed of 1.15 g (4.77 mmol) of 2,3,3a,4-tetrahydro-1H-pyrrolo[2,1-c]-[1,2,4]benzothiadiazin-7-ol 5,5-dioxide, 1.00 g (6.21 mmol) of [4-(cyanomethyl)phenyl]-boronic acid, 1.3 g (7.15 mmol) of copper(II) acetate, 1.16 ml (14.31 mmol) of pyridine and about 500 mg of 4 Å molecular sieve in 200 ml of methylene chloride is stirred overnight. The reaction mixture is diluted by adding a further 100 ml of methylene chloride and the suspension is filtered. The filtrate is concentrated and then directly placed on a silica column which is eluted with a methylene chloride/methanol 99/1 system. The fractions containing the expected product are combined and evaporated, and the residue is taken up in a small amount of ethyl ether. After filtering off the solid, the title product is obtained in the form of beige powder.

Melting point: 156-158° C.

Step B: 7-[4-(1H-Tetrazol-5-ylmethyl)phenoxy]-2,3,3a,4-tetrahydro-1H-pyrrolo-[2,1-c][1,2,4]benzothiadiazine 5,5-dioxide A suspension of 300 mg (0.844 mmol) of the product obtained in Step A, 164 mg (2.53 mmol) of sodium azide and 113 mg (2.11 mmol) of $NH_4Cl$ in 3 ml of DMF is stirred at 110° C. for 24 hours. The reaction mixture is allowed to return to ambient temperature and is poured into 20 ml of 1N HCl. Extraction (AcOEt), drying ($MgSO_4$) and evaporating to dryness are carried out. The residue is triturated in $Et_2O$ and the precipitate is filtered off to yield the title product.

Melting point: 209-212° C. Elemental micro-analysis:

|  | C | H | N | S |
|---|---|---|---|---|
| Theoretical % | 54.26 | 4.55 | 21.09 | 8.05 |
| Empirical % | 54.18 | 4.44 | 20.67 | 8.05 |

EXAMPLE 28

3-{4-[(5,5-Dioxido-2,3,3a,4-tetrahydro-1H-pyrrolo[2,1-c][1,2,4]-benzothiadiazin-7-yl)oxy]benzyl}-1,2,4-oxadiazole-5(4,H)-thione Step A: 2-{4-[(5,5-Dioxido-2,3-dihydro-1H-pyrrolo[2,1-c][1,2,4]benzothiadiazin-7-yl)oxy]phenyl}-N'-hydroxyethanimidamide 2.51 ml (18.0 mmol) of triethylamine are added to a solution of 1.25 g (18.0 mmol) of hydroxylamine hydrochloride in 4 ml of DMSO and the suspension is stirred for 10 minutes. The precipitate is filtered off and the filtrate is concentrated. 992 mg (3.00 mmol) of the product of Step A of Example 27 are added to the filtrate and the solution is stirred at 75° C. for 1 hour 30 minutes. The solution is allowed to return to ambient temperature, and precipitation of the reaction mixture is brought about using water. The precipitate is filtered off to yield the title product.

Step B: 3-{4-[(5,5-Dioxido-2,3-dihydro-1H-pyrrolo[2,1-c][1,2,4]benzothiadiazin-7-yl)oxy]benzyl}-1,2,4-oxadiazole-5(4H)-thione 348 mg (1.95 mmol) of 1,1'-thiocarbonyldiimidazole and then 530 µl (3.516 mmol) of DBU are added to a suspension of the product obtained in Step A (330 mg, 0.85 mmol) in 8 ml of $CH_3CN$. The reaction solution is stirred at ambient temperature overnight. 20 ml of 1N HCl are added; extraction ($CH_2Cl_2$), washing (saturated NaCl), drying ($MgSO_4$) and evaporating to dryness are carried out. The title product is obtained in the form of a yellow wax which is used in the crude state in the following Step.

Step C: 3-{4-[(5,5-Dioxido-2,3,3a,4-tetrahydro-1H-pyrrolo[2,1-c][1,2,4]-benzothiadiazin-7-yl)oxy]benzyl}-1,2,4-oxadiazole-5(4H)-thione The product obtained in Step B (290 mg, 0.68 mmol) in ethanol (12 ml) in the presence of $NaBH_4$ (77 mg, 2.03 mmol) is stirred at ambient temperature for 1 hour. 10 ml of 1N HCl are added and extraction ($CH_2Cl_2$) is carried out. The title product is purified by chromatography on a silica column ($CH_2Cl_2$/MeOH 99/1).

Melting point: 124-126° C. Elemental micro-analysis:

|  | C | H | N | S |
|---|---|---|---|---|
| Theoretical % | 53.01 | 4.21 | 13.01 | 14.90 |
| Empirical % | 53.05 | 4.37 | 12.32 | 15.20 |

EXAMPLE 29

N-(1-{4-[(5,5-Dioxido-2,3,3a,4-tetrahydro-1H-pyrrolo[2,1-c][1,2,4]-benzothiadiazin-7-yl)oxy]phenyl}ethyl)methanesulphonamide Step A: 1-{4-[(5,5-Dioxido-2,3,3a,4-tetrahydro-1H-pyrrolo[2,1-c][1,2,4]benzothiadiazin-7-yl)oxy]phenyl}ethanone A suspension composed of 3.0 g (12.48 mmol) of 2,3,3a,4-tetrahydro-1H-pyrrolo[2,1-c]-[1,2,4]benzothiadiazin-7-ol 5,5-dioxide, 3.18 g (18.73 mmol) of (4-acetylphenyl)boronic acid, 3.42 g (18.82 mmol) of copper(II) acetate, 3.03 ml (37.15 mmol) of pyridine and about 500 mg of 4 Å molecular sieve in 150 ml of methylene chloride is stirred overnight. The reaction mixture is diluted by adding a further 100 ml of methylene chloride and the suspension is filtered. The filtrate is concentrated and then directly placed on a silica column which is eluted with a $CH_2Cl_2$/acetone 99/1 system. The fractions containing the expected product are combined and evaporated, and the residue is taken up in ethyl ether. After filtering off the solid, the title product is recovered in the form of white powder.

Melting point: 152-154° C.

Step B: (1-{4-[(5,5-Dioxido-2,3,3a,4-tetrahydro-1H-pyrrolo[2,1-c][1,2,4]benzothiadiazin-7-yl)oxy]phenyl}ethyl)amine 1.65 ml (5.63 mmol) of titanium(IV) isopropoxide are added dropwise to a solution of 1.0 g (2.80 mmol) of the product obtained in Step A in 5 ml of 7N ammoniacal methanol. Stirring is carried out at ambient temperature overnight, 424 mg (11.20 mmol) of $NaBH_4$ are added and stirring is continued for 2 hours. Precipitation of the reaction mixture is brought about by adding water (2-3 ml); a white precipitate is filtered off. The filtrate is set aside. The precipitate is suspended in AcOEt, stirring is carried out for 30 minutes and filtration is carried out. The filtrate is combined with the first filtrate and the extraction with AcOEt is repeated. The organic phases are combined, washed (saturated NaCl), dried ($MgSO_4$) and evaporated in vacuo to yield the title product.

Step C: N-(1-{4-[(5,5-Dioxido-2,3,3a,4-tetrahydro-1H-pyrrolo[2,1-c][1,2,4]benzothiadiazin-7-yl)oxy]phenyl}ethyl)methanesulphonamide The procedure is as in Example 2, using the product of Step B above as starting material.

Melting point: 122-127° C. Elemental micro-analysis:

|  | C | H | N | S |
|---|---|---|---|---|
| Theoretical % | 52.16 | 5.30 | 9.60 | 14.66 |
| Empirical % | 51.93 | 5.81 | 9.32 | 14.59 |

EXAMPLE 30

N-(1-{3-[(5,5-Dioxido-2,3,3a,4-tetrahydro-1H-pyrrolo[2,1-c][1,2,4]-benzothiadiazin-7-yl)oxy]phenyl}ethyl)methanesulphonamide The procedure is as in Steps A, B and C of Example 29, replacing the (4-acetylphenyl)-boronic acid in Step A by (3-acetylphenyl)boronic acid.

Melting point: 83-84° C. Elemental micro-analysis:

|  | C | H | N | S |
|---|---|---|---|---|
| Theoretical % | 52.16 | 5.30 | 9.60 | 14.66 |
| Empirical % | 52.03 | 5.28 | 9.20 | 14.81 |

EXAMPLE 31

N-{4-[(5,5-Dioxido-2,3,3a,4-tetrahydro-1H-pyrrolo[2,1-c][1,2,4]-benzothiadiazin-7-yl)oxy]benzyl}-N-methylmethanesulphonamide A suspension composed of 5.74 mg (3.37 mmol) of 2,3,3a,4-tetrahydro-1H-pyrrolo[2,1-c]-[1,2,4]benzothiadiazin-7-ol 5,5-dioxide, 926 mg (4.04 mmol) of (4-{[methyl(methylsulphonyl)amino]methyl}phenyl)boronic acid, 920 mg (5.06 mmol), of copper(II) acetate, 817 µl (10.10 mmol) of pyridine and about 4 g of 4 Å molecular sieve in 50 ml of $CH_2Cl_2$ is stirred overnight. The reaction mixture is filtered, rinsing with $CH_2Cl_2$/MeOH (1/1). The filtrate is concentrated and then directly placed on a silica column which is eluted with a $CH_2Cl_2$/MeOH 95/5 system. The fractions containing the expected product are combined and evaporated, and the residue is taken up in ethyl ether. After filtering off the solid, the title product is recovered in the form of white powder.

Melting point: 142-144° C. Elemental micro-analysis:

|  | C | H | N | S |
|---|---|---|---|---|
| Theoretical % | 52.16 | 5.30 | 9.60 | 14.66 |
| Empirical % | 51.99 | 5.55 | 9.43 | 14.86 |

EXAMPLE 32

{3-[(5,5-Dioxido-2,3,3a,4-tetrahydro-1H-pyrrolo[2,1-c][1,2,4]-benzothiadiazin-7-yl)oxy]benzyl}dimethylamine Step A: Methyl 3-[(5,5-Dioxido-2,3-dihydro-1H-pyrrolo[2,1-c][1,2,4]benzothiadiazin-7-yl)oxy]benzoate The procedure is as in Step B of Example 1, using the compound obtained in Step A of Example 1 and [3-(methoxycarbonyl)phenyl]boronic acid as starting materials.

Melting point: 211-214° C. Elemental micro-analysis:

|  | C | H | N | S |
|---|---|---|---|---|
| Theoretical % | 58.06 | 4.33 | 7.52 | 8.61 |
| Empirical % | 57.70 | 4.54 | 7.29 | 8.37 |

Step B: 3-[3-(Aminosulphonyl)-4-(2-oxopyrrolidin-1-yl)phenoxy]benzoic acid

A suspension of the product obtained in Step A (1.1 g, 2.55 mmol) in 18 ml of 1N NaOH is heated at 95° C. until a solution is obtained. The solution is allowed to return to ambient temperature, is acidified with 1N HCl and extracted (CH$_2$Cl$_2$). The organic phases are combined, washed (saturated NaCl), dried (MgSO$_4$) and evaporated. The residue is triturated in Et$_2$O; the title product precipitates out and is recovered by filtration.

Step C: 3-[(2,3-Dihydro-5,5-dioxido-1H-pyrrolo[2,1-c][1,2,4]benzothiadiazin-7-yl)-oxy]benzoic acid A suspension of the product obtained in Step B (850 mg, 2.26 mmol) in 25 ml of THF in the presence of 675 µl (4.52 mmol) of DBU is refluxed for 1 hour. It is allowed to return to ambient temperature and is acidified with 1N HCl, and the white precipitate corresponding to the title product is filtered off. Elemental micro-analysis:

|  | C | H | N | S |
|---|---|---|---|---|
| Theoretical % | 56.98 | 3.94 | 7.82 | 8.95 |
| Empirical % | 57.15 | 4.13 | 7.68 | 9.16 |

Step D: 3-[(5,5-Dioxido-2,3-dihydro-1H-pyrrolo[2,1-c][1,2,4]benzothiadiazin-7-yl)-oxy]-N,N-dimethylbenzamide:

To a suspension of the product obtained in Step C (1.40 g, 3.91 mmol) in 20 ml of CH$_2$Cl$_2$ there are added 2 drops of DMF and then, dropwise, 684 µl (7.81 mmol) of oxalyl chloride diluted with 2 ml of CH$_2$Cl$_2$. Stirring is carried out at ambient temperature for 2 hours 30 minutes; evaporation to dryness is carried out; the residue is taken up in 15 ml of CH$_2$Cl$_2$; 1.1 ml (7.81 mmol) of Et$_3$N and then 2.94 ml (5.87 mmol) of a 2M solution of dimethylamine in THF are added. Stirring is carried out at ambient temperature for 1 hour. The reaction mixture is acidified with 0.5N HCl and extracted (CH$_2$Cl$_2$). The organic phases are combined, washed (saturated NaCl), dried (MgSO$_4$) and evaporated. The residue is triturated in Et$_2$O; the title product precipitates out and is recovered by filtration. Elemental micro-analysis:

|  | C | H | N | S |
|---|---|---|---|---|
| Theoretical % | 59.21 | 4.97 | 10.90 | 8.32 |
| Empirical % | 59.23 | 5.09 | 10.47 | 7.97 |

Step E: {3-[(5,5-Dioxido-2,3,3a,4-tetrahydro-1H-pyrrolo[2,1-c][1,2,4]benzothiadiazin-7-yl)oxy]benzyl}dimethylamine 3.72 ml (3.72 mmol) of a 1M solution of LiAlH$_4$ in THF are added dropwise to a suspension of 577 mg (1.49 mmol) of the product obtained in Step D in 20 ml of THF. The reaction mixture is observed passing into solution and stirring is carried out at ambient temperature for 3 hours. The excess of hydride is hydrolysed by the dropwise addition of water until the evolution of gas ceases. The suspension is stirred for 10 minutes, 20 ml of water are added, and extraction is carried out with AcOEt. The organic phases are combined, washed (saturated NaCl), dried (MgSO$_4$) and evaporated, and the residue is chromatographed on a silica column (CH$_2$Cl$_2$/MeOH 95/5) to yield the title product.

Melting point: 122° C. Elemental micro-analysis:

|  | C | H | N | S |
|---|---|---|---|---|
| Theoretical % | 61.10 | 6.21 | 11.25 | 8.59 |
| Empirical % | 61.32 | 6.19 | 11.06 | 8.52 |

Pharmacological Study of Products of the Invention

Study of the Excitatory Currents Induced by AMPA in *Xenopus oocytes* a—Method:

mRNA's are prepared from cerebral cortex of male Wistar rats by the guanidinium thiocyanate/phenol/chloroform method. The poly (A$^+$) mRNA's are isolated by chromatography on oligo-dT cellulose and injected at a level of 50 ng per oocyte. The oocytes are incubated for 2 to 3 days at 18° C. to permit expression of the receptors and are then stored at 8-10° C.

Electrophysiological recording is carried out in a Plexiglass® chamber at 20-24° C. in OR2 medium (J. Exp. Zool., 1973, 184, 321-334) by the "voltage-clamp" method using two electrodes, with a third electrode placed in the bath serving as reference.

All the compounds are applied via the incubation medium and the electric current is measured at the end of the application period. AMPA is used in a concentration of 10 µM. For each compound studied, the concentration that doubles (EC2×) or quintuples (EC5×) the intensity of the current induced by AMPA alone (5 to 50 nA) is determined.

b—Results:

The compounds of the invention potentiate the excitatory effects of AMPA to a very considerable degree and their activity is very clearly superior to that of compounds of reference. The compound of Example 1 especially has an EC2× of 3.5 µM and an EC5× of 9.2 µM, the compound of Example 2 an EC2× of 0.35 μM and an EC5× of 2.6 μM, and the compound of Example 21 an EC2× of 0.1 μM and an EC5× of 0.56 μM.

PHARMACEUTICAL COMPOSITION

| Formula for the preparation of 1000 tablets each containing 100 mg of N-{3-[(5,5-dioxido-2,3,3a,4-tetrahydro-1H-pyrrolo[2,1-c][1,2,4]benzothiadiazin-7-yl)oxy]benzyl}methanesulphonamide (Example 2) | 100 g |
|---|---|
| hydroxypropylcellulose | 2 g |
| wheat starch | 10 g |
| lactose | 100 g |
| magnesium stearate | 3 g |
| talc | 3 g |

We claim:

1. A compound selected from those of formula (I):

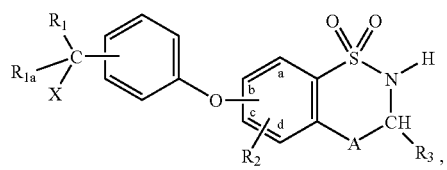

wherein:
R$_1$ represents hydrogen, halogen, or linear or branched (C$_1$-C$_6$)alkyl,
R$_{1a}$ represents hydrogen or linear or branched (C$_1$-C$_6$) alkyl,
R$_2$ represents hydrogen, halogen, or hydroxy,
A represents NR$_4$, and R$_3$ and R$_4$, together with the carbon and nitrogen atoms to which they are attached, form a ring

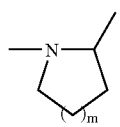

wherein m represents 1, 2, or 3,
X represents NR$_6$R$_7$, S(O)$_n$R$_8$, or OR'$_8$, or a heterocyclic group, wherein:
R$_6$ represents hydrogen, linear or branched (C$_1$-C$_6$) alkyl, S(O)$_p$R$_9$, COR$_9$, or P(O)OR$_9$OR$_{10}$,
R$_7$ represents hydrogen, or linear or branched (C$_1$-C$_6$) alkyl,
or R$_6$ and R$_7$, together with the nitrogen atom carrying them, form a heterocyclic group,
R$_8$, R$_9$ and R$_{10}$, which may be the same or different, represent hydrogen; linear or branched (C$_1$-C$_6$)alkyl optionally substituted by one or more halogen; aryl-(C$_1$-C$_6$)alkyl in which the alkyl moiety is linear or branched; or aryl,
R'$_8$ represents linear or branched (C$_1$-C$_6$)alkyl or linear or branched (C$_1$-C$_6$)acyl,
n and p, which may be the same or different, represent 1 or 2,
its enantiomers and diastereoisomers, and addition salts thereof with a pharmaceutically-acceptable acid or base.

2. A compound according to claim 1, wherein R$_2$ represents hydrogen.

3. A compound according to claim 1, wherein the group

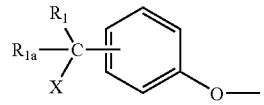

is in position b of the phenyl ring carrying it.

4. A compound according to claim 1, wherein X is NR$_6$R$_7$, or S(O)$_n$R$_8$, or a heterocyclic group.

5. A compound according to claim 1, wherein X is NR$_6$R$_7$.

6. A compound according to claim 1, wherein

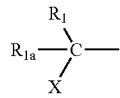

is in the meta-position of the phenoxy ring structure carrying it.

7. A compound according to claim 1, wherein

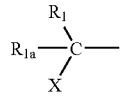

is in the para-position of the phenoxy ring structure carrying it.

8. A compound according to claim 1, wherein m represents 1.

9. A compound according to claim 1, which is selected from {3-[(5,5-dioxido-2,3,3a,b 4-tetrahydro-1H-pyrrolo[2,1-c][1,2,4]benzothiadiazin-7-yl)oxy]phenyl}methanamine, its enantiomers and diastereoisomers, and addition salts thereof with a pharmaceutically-acceptable acid or base.

10. A compound according to claim 1, which is selected from N-{3-[(5,5-dioxido-2,3,3a,4-tetrahydro-1H-pyrrolo[2,1-c][1,2,4]benzothiadiazin-7-yl)oxy]benzyl}methane-sulphonamide, its enantiomers and diastereoisomers, and addition salts thereof with a pharmaceutically-acceptable acid or base.

11. A compound according to claim 1, which is selected from N-{4-[(5,5-dioxido-2,3,3a4-tetrahydro-1H-pyrrolo[2,1-c][1,2,4]benzothiadiazin-7-yl)oxy]benzyl}methane-sulphonamide, its enantioniers and diasterecisomers, and addition salts thereof with a pharmaceutically-acceptable acid or base.

12. A method for treating a living animal body, including a human, afflicted with a condition selected from anxiety and depression, comprising the step of administering to the living animal body, including a human, an amount of a compound of claim 1 which is effective for alleviation of the condition.

13. A pharmaceutical composition comprising as active principle an effective amount of a compound of claim 1, together with one or more pharmaceutically-acceptable excipients or vehicles.

* * * * *